(12) United States Patent
Shimizu et al.

(10) Patent No.: US 6,258,575 B1
(45) Date of Patent: Jul. 10, 2001

(54) HYDROLYZING FATS AND OILS USING AN IMMOBILIZED ENZYME COLUMN AND SUBSTRATE-FEEDING CHAMBER THAT SEPARATES PHASES

(75) Inventors: Masami Shimizu; Toshiteru Komatsu; Naoto Yamada, all of Ibaraki (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/448,140

(22) Filed: Nov. 24, 1999

(30) Foreign Application Priority Data

Nov. 26, 1998 (JP) .................................. 10-335164
Apr. 14, 1999 (JP) .................................. 11-106607

(51) Int. Cl.$^7$ ...................................... C12P 7/64
(52) U.S. Cl. ..................... 435/134; 435/177; 435/180; 435/289.1
(58) Field of Search ................... 435/134, 174, 435/177, 180, 289.1

(56) References Cited

FOREIGN PATENT DOCUMENTS

| | | |
|---|---|---|
| 58-146284 | 8/1983 | (JP) . |
| 61-085195 | 4/1986 | (JP) . |
| 63-059896 | 3/1988 | (JP) . |
| 1-098494 | 4/1989 | (JP) . |
| 4-335881 | 11/1992 | (JP) . |

OTHER PUBLICATIONS

Yoshitsugu Kosugi, et al., "Continuous Lipolysis Reactor with a Loop Connecting an Immobilized Lipase Column and an Oil–Water Separator[1]", JAOCS, vol. 72, No. 11, 1995, pp. 1329–1332.

*Primary Examiner*—David M. Naff
(74) *Attorney, Agent, or Firm*—Oblon, Spivak, McClelland, Maier & Neustadt, P.C.

(57) ABSTRACT

An oil or fat phase is provided above an aqueous phase in a substrate-feeding chamber such that there is a distinct interface between the phases. The phases are separately removed from the chamber, mixed together and fed to an immobilized-enzyme reaction column to produce a reaction mixture. The mixture is fed to the substrate-feeding chamber and introduced into the oil or fat phase such that the interface remains distinct and undisturbed, and monoglycerides, diglycerides and fatty acids remain in the oil or fat phase and water and glycerol separate into the aqueous phase. Steps of the process are repeated while maintaining the interface distinct and undisturbed in the substrate-feeding chamber until a desired degree of oil or fat hydrolysis is obtained. The mixture from the reaction column may be fed to a mixing chamber, mixed with water from the substrate-feeding chamber, and fed to the substrate-feeding chamber. In another embodiment, only the oil or fat phase is fed to the reaction column to produce a reaction mixture that is fed to the mixing chamber and then to the substrate-feeding chamber. The process provides a high degree of hydrolysis due to adequate extraction of glycerol.

17 Claims, 2 Drawing Sheets

HYDROLYZING FATS AND OILS USING AN IMMOBILIZED ENZYME COLUMN AND SUBSTRATE-FEEDING CHAMBER THAT SEPARATES PHASES

BACKGROUND OF THE INVENTION

1. Field of the Invention

The present invention relates to a process for efficiently hydrolyzing fats and oils to produce aliphatic acids. In particular, the present invention relates to a process for efficiently hydrolyzing fats and oils without the reduction of enzyme activity caused by an increase in the number of treatments. In the description, the term of "fats and oils" may mean an inclusion of a fat, an oil, a lard, a grease, and so on.

2. Description of the Background

As continuous processes for hydrolyzing fats and oils by an enzyme, there are processes wherein an lipolytic enzyme (lipase) is immobilized onto resin or membrane and used in a circulating reactor such as a batch stirring multi-stage reactor, a packed column or a membrane reactor and an oily substrate and a water-soluble substrate are circulated in countercurrent or cocurrent (JP-A 61-85195, JP-A 63-59896 and JP-A 1-98494). In any methods, however, apparatuses are complicated and the method of operating an enzyme column is very difficult.

As reaction examples in a batch circulating system, e.g. the following techniques are known: (1) a method of conducting a mixture having fats and oils mixed with water in an amount of about 60 weight % relative to the fats and oils to pass through an enzyme-packed reactor; (2) a method of conducting only fats and oils not containing an aqueous phase substrate to pass through a lipase immobilized on polysaccharide gel containing a large amount of water (JP-A 58-146284); (3) a method of mixing fats and oils with water uniformly by circulating them through a fat- and oil-storing tank and a humidifying apparatus and then conducting the mixture with the water content kept constant to pass through an enzyme-packed reactor (JP-A 4-335881); and (4) a method of introducing fats, oils, and water to a substrate-circulating chamber, feeding the oil phase substrate only to an enzyme column while the oil phase is separated from the aqueous phase, and returning the discharged reaction solution to the bottom of the substrate-circulating chamber (Kosugi, Y., Tomizuka, N., J. Am. Oil. Chem. Soc. 72;1329 (1995)).

In the process for hydrolyzing fats and oils by an enzyme, it is desired that the enzyme is not lost while attaining a sufficient reaction rate in easy operation in simple facilities and also that an oil phase product and an aqueous phase product can be separated from each other without centrifugation or a membrane.

Further, the above-described method (1) has the problem that because the enzyme is removed with time, the enzyme activity is lowered as the number of treatments is increased, although the degree of hydrolysis is high due to a high water content in the mixture. In the method (2) unlike the method (1), the enzyme is not removed with time, but water being necessary for hydrolysis tends to be insufficient while glycerol is accumulated in the immobilized enzyme, thus shifting the equilibrium to the side of fats and oils, which may result in inadequate decomposition of fats and oils. In the method (3), separation of the oil phase from the aqueous phase after decomposition (or hydrolysis) is difficult thus making a separation step and facilities therefor necessary and incidental. Further, any method of the methods (1) to (3) suffers from the problem that the apparatuses are complicated or the enzyme-packed reactor is very difficult to operate. In the method (4), the water content in the oil phase passing through the enzyme reactor is low and the separation of the oil phase from the aqueous phase after decomposition (or hydrolysis) is easy, but there is the problem that it is difficult to obtain high degrees of decomposition due to inadequate extraction of glycerol from the reaction solution.

SUMMARY OF THE INVENTION

The present inventors have found a process in which an immobilized enzyme is used for recovery of the enzyme and while the oil phase and the aqueous phase are separated from each other naturally in a substrate-feeding chamber, the reaction is repeatedly conducted thereby solving the conventionally problematic reaction rate and separation of products, and further because the apparatuses consisting of only an enzyme column and a substrate-feeding chamber, the facilities are simple and operation are used easily to be able to achieve stable operation, and simultaneously the investment for the facilities are economical.

Another object of the present invention is to provide a process for efficiently hydrolyzing fats and oils in easy operation at high degrees of hydrolysis without lowering enzyme activity with time.

In addition, the present inventors have found that after the oil and water are separated in the substrate-feeding chamber, the water content in the oil phase substrate fed to the enzyme column is made up to have sufficient amount whereby the hydrolysis reaction in the enzyme column is promoted, and thereafter the reaction solution is brought into contact with a sufficient amount of water whereby the glycerol formed by hydrolysis is dissolved so that the reaction is prevented from being shifted to the side of fats and oils, whereby the hydrolysis can be conducted sufficiently, the apparatus used is made simpler, and the operation is made easier.

The present invention relates to a process for hydrolyzing fats and oils, which comprises using an enzyme column (reaction column) using an immobilized enzyme and a substrate-feeding chamber also serving as an oil-water separating chamber, circulating a reaction solution between the enzyme column and the substrate-feeding chamber and simultaneously separating oils from water in the substrate-feeding chamber, wherein an oil phase substrate and an aqueous phase substrate are removed separately without previously mixing them in the substrate-feeding chamber, and then the hydrolysis of fats and oils is conducted in any of the following processes:

1) a process for hydrolyzing fats and oils, which comprises mixing an oil phase substrate with an aqueous phase substrate and feeding the mixture to the enzyme column;
2) a process for hydrolyzing fats and oils, which comprises mixing an oil phase substrate with an aqueous phase substrate, feeding the mixture to the enzyme column, and introducing a reaction solution having passed through the enzyme column into a mixing chamber for bringing the reaction solution into contact with an aqueous phase substrate, and bringing the reaction solution into contact with the aqueous phase substrate in said mixing chamber, while, after that, returning the mixture to the substrate-feeding chamber; and
3) a process for hydrolyzing fats and oils, which comprises feeding only an oil phase substrate to the enzyme column, introducing a reaction solution having passed through the enzyme column into a mixing chamber for bringing the reaction solution into contact with an aqueous phase substrate and bringing the reaction solution into contact with the aqueous phase substrate in said mixing chamber, while, after that, returning the mixture to the substrate-feeding chamber.

Preferably, an oil-water interface can be formed during reaction in the substrate-feeding chamber. The water content in the oil phase substrate after separation of oils and water is preferably from the saturated one to 5%.

The aqueous phase substrate can be fed from the substrate-feeding chamber to the oil-water mixing chamber.

Preferably, the reaction solution is brought into contact with the aqueous phase substrate by stirring or in a countercurrent contacting system in the oil-water mixing chamber.

In addition, the present invention comprises conducting an oil phase and an aqueous phase to be separated in the feeding chamber without stirring, removing them through respective pipes to bring them into contact with an enzyme, separating the reaction solution flowing from the enzyme column into an oil phase and an aqueous phase in the feeding chamber, and repeating this operation-series, to solve the problem described above. In the present invention, the pipe for returning the reaction solution to the substrate-feeding chamber is attached to be immersed in a separated upper layer so as not to disturb an oil-water interface, and further the flow rate of the circulating reaction solution is regulated. A sufficient reaction rate can thereby be obtained using a packed column with an immobilized enzyme, and a loss of the enzyme can be prevented. Further, by conducting the oil phase and the aqueous phase to be separated from each other by the difference in specific gravity in the feeding chamber, use of any special apparatus for separating oils from water can be eliminated.

Further, the present invention also provides a process for hydrolyzing fats and oils, which comprises feeding a solution of an oil phase substrate from a substrate-feeding chamber to an enzyme column packed with enzyme-immobilized carriers, and bringing the reaction solution having passed through said enzyme column into contact with an aqueous phase substrate in an oil-water mixing chamber, followed by separating the oils from water.

Figure 1:
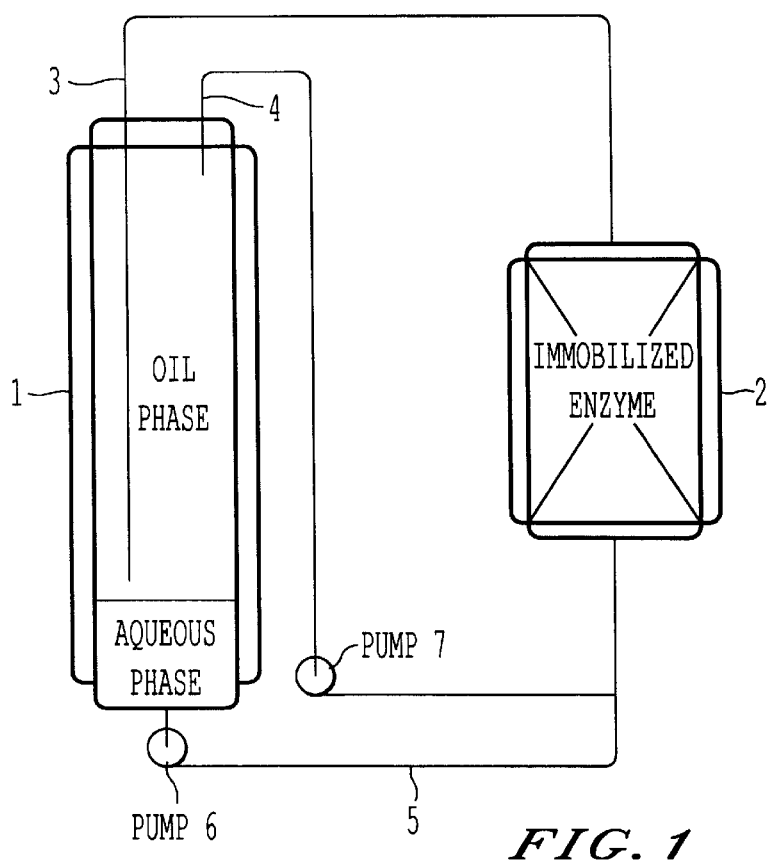
FIG. 1 shows the circulating stationary separable reactor used in the present invention.
Figure 2:
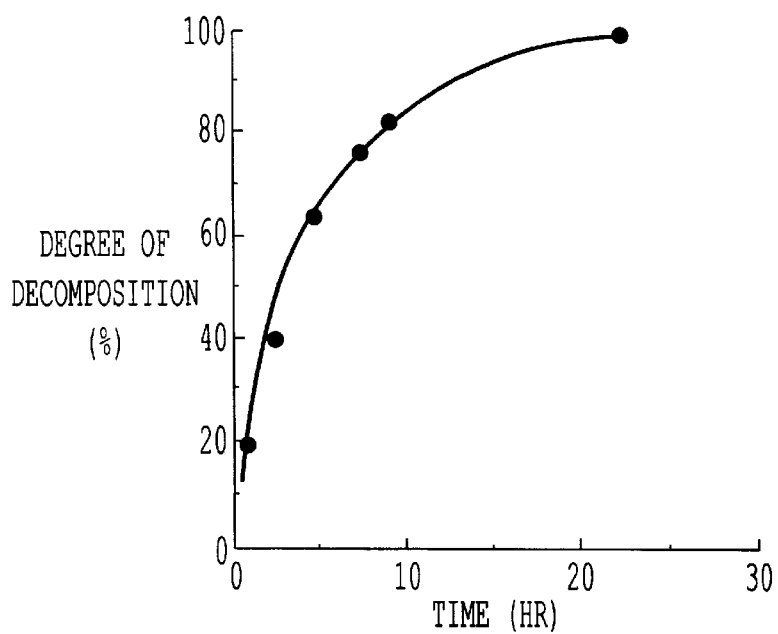
FIG. 2 is a graph showing a change with time of the degree of decomposition of an oil phase in the circulating stationary separable reactor.

The expression of reference letters in FIGS. 1 to 2 are as follows:
1 makes reference of a substrate-feeding chamber (oil-water separating chamber); 2 does an enzyme column; 3 does a reaction solution-returning line; 4 does an oil phase substrate-removing line; 5 does an aqueous phase substrate-removing line; and 6 and 7 do pumps.

Figure 3:
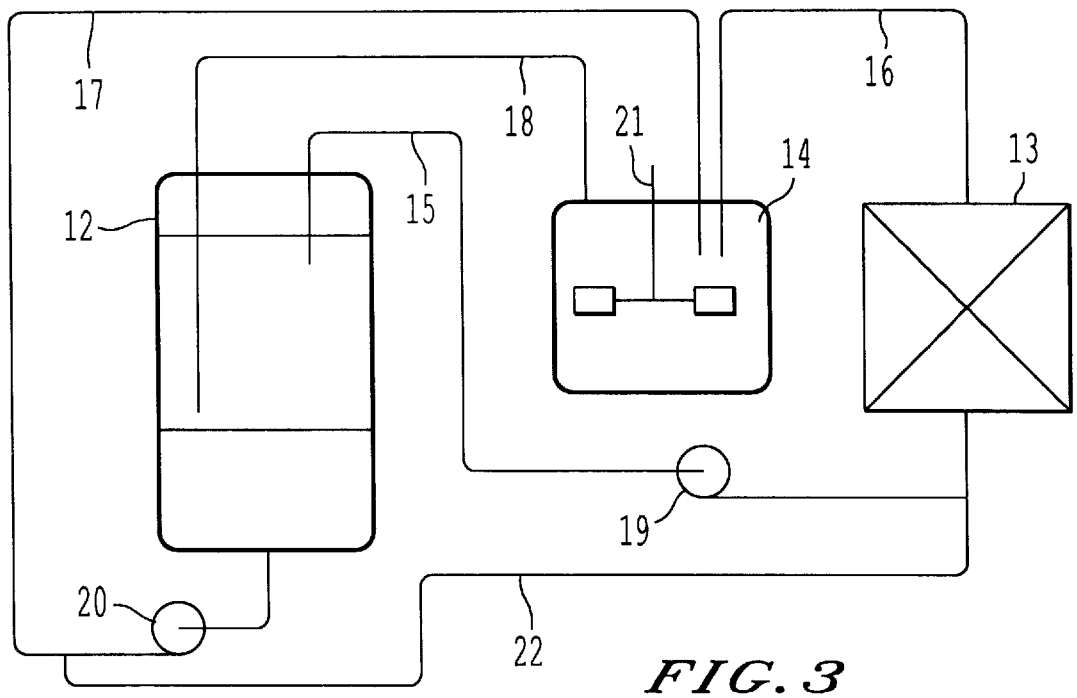

FIG. 3 shows an example of an apparatus for carrying out the process for hydrolyzing fats and oils according to the present invention.

Figure 4:
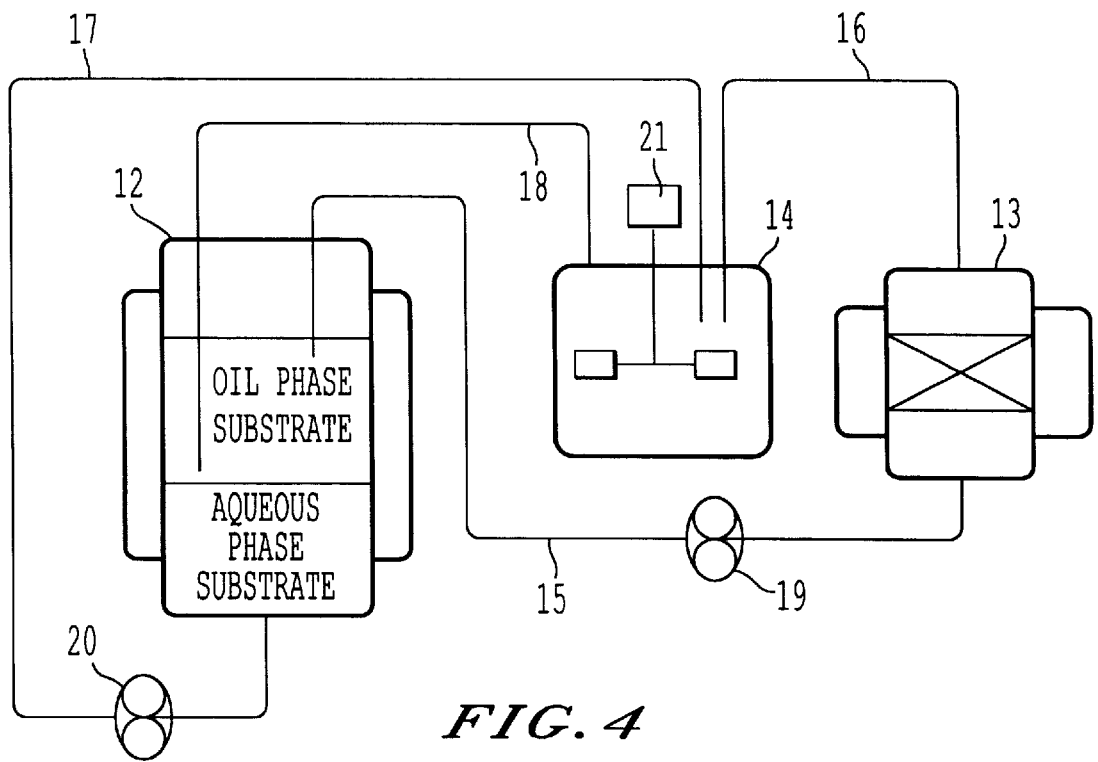

FIG. 4 shows another example of an apparatus for carrying out the process for hydrolyzing fats and oils according to the present invention.

The expression of reference letters in FIGS. 3 to 4 are as follows:
12 makes reference of a substrate-feeding chamber; 13 does an enzyme column; 14 does an oil-water mixing chamber; 15 does an oil phase substrate-removing line; 16 does a reaction solution-discharging line; 17 does an aqueous phase substrate-feeding line; 18 does a reaction solution, aqueous phase mixture-returning line; 19 and 20 do pumps; 21 does a stirrer; and 22 does an aqueous phase substrate-enzyme column feeding line.

DETAILED DESCRIPTION OF THE PREFERRED EMBODIMENTS

The enzyme used in the reaction may be an enzyme immobilized by adsorption onto a carrier. The type of enzyme is not limited insofar as the enzyme hydrolyzes fats and oils, and the enzyme includes e.g. lipase, esterase etc. The method of conducting the enzyme to be adsorbed onto a carrier is not limited, and it is cited as the method described in JP-A 1-153090. The amount of the immobilized enzyme used may be an amount (activity) to meet productivity. The shape of the enzyme column is not limited insofar as the column endures the pressurization of a pump used. Further, the enzyme column is preferably a column which can be heated by a jacket to a suitable temperature for the enzyme reaction.

The substrate-feeding chamber also serving as the oil-water separating chamber does not possess a stirrer. It has pipes for respectively (or separately from each other) removing an oil phase and an aqueous phase separated by being left stationarily and sending them to the enzyme column. Further, it has a pipe for returning a reaction solution flowing from the enzyme column. The oil phase-removing pipe is arranged such that its opening for removal is placed at a position over a middle portion of the oil phase. On the other hand, the aqueous phase-removing pipe is arranged such that its opening for removal is placed at the bottom of the substrate-feeding chamber. Further, the reaction solution-returning pipe is arranged such that its opening for returning is placed at a position so as not to disturb an oil phase-aqueous phase interface. These positions may be regulated as necessary because such positions are also varied depending on the amount of production (flow rate of the reaction solution) and the amount of the enzyme used. Furthermore, the shape (chamber height/chamber diameter etc.) of the substrate-feeding chamber may be designed such that separation of oils from water can be effected satisfactorily. This substrate-feeding chamber is preferably a chamber which can be heated similarly to the enzyme column.

Feeding of the substrate to the enzyme column may be conducted using either a downward stream from the top of the column to the bottom of the column or an upward stream from the bottom of the column to the top of the column, but it is necessary to let flow both the oil and aqueous phase substrates in the same direction. Reaction apparatuses in a countercurrent system have been proposed heretofore, but in a liquid (fats and oils)-liquid (water) type reaction, it is very difficult to make reactants countercurrently pass through a packed column, thus making it necessary to device and complicate the apparatus therefor. Accordingly, in the present invention, a liquid (fats and oils)-liquid (water) are allowed to flow in a cocurrent, that is, in the same direction, mixed at outlets of feeding pumps for oil and aqueous phases and then sent to the enzyme column.

Depending on the substrate to be decomposed, an outlet of a pump may be provided with a mixer such as an in-line mixer. Desired degrees of decomposition can be determined depending on the initial ratio of charged fats, oils and water, the positional selectivity of the enzyme (random type, or α-position-selective type). To obtain high degrees of decomposition, it is necessary to use a random-type immobilized enzyme and to increase the amount of water added. Feeding of oil and aqueous phases to the enzyme column is conducted desirably at the initial charge ratio.

According to the present invention, hydrolysis of fats and oils can be conducted with low investment without a loss in the enzyme. That is, expensive facilities such as a high-pressure decomposition column used in conventional facilities for producing aliphatic acids and a high-pressure boiler for generating heat transfer medium are not necessary, and furthermore the operation is easy due to the batch reaction, and the simplification of the apparatus can be realized.

The formed aliphatic acids may be used as usual raw materials for oleo-chemicals, raw materials for producing foods and raw materials for cosmetics. Further, because the formed sweet water does not contain enzymes or contaminating proteins, it can be used as usual glycerol after concentration and subsequent simple purification.

Now, the present invention "3) a process for hydrolyzing fats and oils, which comprises feeding an oil phase substrate only to the enzyme column, introducing a reaction solution having passed through the enzyme column into a mixing chamber for bringing the reaction solution into contact with an aqueous phase substrate and after the reaction solution is brought into contact with the aqueous phase substrate in said mixing chamber, returning the mixture to the substrate-feeding chamber during which the fats and oils are hydrolyzed" is described.

FIG. 4 shows an example of an apparatus for carrying out the present method.

In the process of the present invention, the solution of oil phase substrate is first fed from the substrate-feeding chamber in which the oil phase substrate and the aqueous phase substrate are accommodated, to the enzyme column charged with enzyme-immobilized carriers. The oil phase substrate is a mixture of triglycerides, diglycerides, monoglycerides, free aliphatic acids etc., preferably fats and oils, and particularly preferably it further contains a very small amount of water because the presence of water is necessary for hydrolysis. However, it is not preferable that the oil phase substrate contains a large amount of water because the immobilized enzyme is left (or removed) with time to lower the enzyme activity. Accordingly, the water content in the oil phase substrate is preferably from saturation solubility (maximum amount of water dissolved in the oil phase substrate) to 5% by weight (hereinafter referred to simply as "%"), more preferably saturation solubility to 4%, particularly preferably saturation solubility to 3%. According to the present method, the water content in the oil phase substrate can be made saturation solubility to 5% by bringing the oil phase substrate into contact with the aqueous phase substrate upon accommodation of both the substrates in the substrate-feeding chamber or by bringing the aqueous phase substrate into contact with the reaction solution as described below. The aqueous phase substrate is a mixture of water and water-soluble materials such as glycerol, and it is preferably water. The water may be tap water, well water, distilled water and deionized water, and deionized water is particularly preferable.

To feed such an oil phase substrate, it is preferable that the both phases are separated from each other in the substrate-feeding chamber without adding shearing force such as stirring. Further, the end (or terminal), at the side of the substrate-feeding chamber, of the oil phase substrate-removing line for feeding the oil phase substrate from the substrate-feeding chamber to the enzyme column is arranged preferably in the vicinity of the top surface of the oil phase substrate in the substrate-feeding chamber. The flow rate of the oil phase substrate can be determined suitably in consideration of the throughput capacity of the enzyme. Further, feeding of the oil phase substrate to the enzyme column may be conducted using either an upward stream from the bottom of the column to the top of the column or a downward stream from the top of the column.

The oil phase substrate sent to the enzyme column is decomposed with the immobilized enzyme in the enzyme column to form diglycerides, monoglycerides, fatty acids and glycerol. If the water content in the oil phase substrate is very small, the immobilized enzyme is not left (or removed) from the carriers, while the glycerol in the reaction solution after passing through the enzyme column is transferred to the aqueous phase substrate in the oil-water mixing chamber, so the reaction is not shifted to the side of fats and oils, and the degree of decomposition of fats and oils can thereby be raised.

Then, the reaction solution discharged from the enzyme column is brought into contact with the aqueous phase substrate in the oil-water mixing chamber provided separately from the substrate-feeding chamber. By such contact, the diglycerides and monoglycerides and fatty acids remain in the oil phase substrate while the glycerol is transferred to the aqueous phase substrate, and due to the shearing force upon this contact, a very small amount of water is contained in the oil phase substrate.

In the case of bringing the reaction solution into contact with the aqueous phase substrate in the oil-water mixing chamber, it is preferable that the oil-water mixing chamber is stirred, or the aqueous phase substrate as a downward stream from the top of the chamber to the bottom of the chamber is brought into contact with a countercurrent of the reaction solution as an upward stream from the bottom of the chamber to the top of the chamber, or both the means are combined, so that the reaction solution can be sufficiently brought into contact with the aqueous phase substrate. Then, a mixture of the reaction solution and the aqueous phase substrate in the oil-water mixing chamber is sent to the substrate-feeding chamber. Too high shearing force added to the oil-water interface in the substrate-feeding chamber leads to a very large amount of water in the oil phase substrate, so it is preferable that the end (or terminal), at the side of the substrate-feeding chamber, of the reaction solution- aqueous phase substrate mixture-returning line is arranged in the vicinity of the oil-water interface in the substrate-feeding chamber. Because of the capacity of the substrate-feeding chamber and from an economical viewpoint, it is preferable that the aqueous phase substrate in the substrate-feeding chamber is fed to the oil-water mixing chamber. In a particularly preferable method, the aqueous phase substrate in the substrate-feeding chamber is continuously fed to the oil-water mixing chamber, and the reaction solution and the aqueous phase substrate over-flowed from the oil-water mixing chamber are returned to the substrate-feeding chamber.

Then, the oil phase substrate and the aqueous phase substrate are separated from each other by being left stationarily in the substrate-feeding chamber or by centrifugation. In the case of centrifugation, a centrifuge is arranged in a line before the substrate-feeding chamber, and the oil phase substrate and the aqueous phase substrate which were separated from each other are fed preferably through respective lines to the substrate-feeding chamber.

As a result of such a process, a very small amount of water besides fats and oils as well as products decomposed fats and oils such as diglycerides etc. is present in the oil phase substrate in the substrate-feeding chamber because of its contact with the aqueous phase substrate. If the above process is further repeated continuously, hydrolysis of fats and oils further proceeds due to the presence of a very small amount of water in the oil phase substrate, whereby the fats and oils can be decomposed to desired degrees of decomposition.

In the present invention, "2) a process for hydrolyzing fats and oils, which comprises mixing an oil phase substrate with an aqueous phase substrate, feeding the mixture to the enzyme column, introducing a reaction solution having passed through the enzyme column into a mixing chamber for bringing the reaction solution into contact with an aqueous phase substrate, and after the reaction solution is brought into contact with the aqueous phase substrate in said mixing chamber, returning the mixture to the substrate-feeding chamber during which the fats and oils are hydrolyzed" can be conducted with e.g. the apparatus shown in FIG. 3.

This is a modified version of "3) a process for hydrolyzing fats and oils, which comprises feeding an oil phase substrate only to the enzyme column, introducing a reaction solution having passed through the enzyme column into a mixing chamber for bringing the reaction solution into contact with an aqueous phase substrate and after the reaction solution is brought into contact with the aqueous phase substrate in said mixing chamber, returning the mixture to the substrate-feeding chamber during which the fats and oils are hydrolyzed" according to the present invention, and the aqueous phase substrate in the substrate-feeding chamber is fed continuously to both the oil-water mixing chamber and the enzyme column.

EXAMPLES

Example 1

24 g of lipase prepared by immobilizing a commercial lipase (Lipase OF, Meito Sangyo Co., Ltd.) onto ion-exchange resin (Duolite A-568, Diamond Shamrock Co., Ltd.) was charged in stainless steel column 2 (having 22 mm of inner diameter and 150 mm of charge height) equipped with a jacket.

On the other hand, 160 g of soybean oil was added to glass vessel 1 (having 40 mm of inner diameter and 300 mm of height) equipped with a jacket. Hot water at 40° C. was circulated through substrate-feeding chamber 1 and a jacket in enzyme column 2 such that the reaction temperature reached 40° C.

The soybean oil was fed (, sent or charged) using pump 7 to the enzyme column at a flow rate of 5 g/min., and when the oil was flow-out (or discharged) from the returning line 3, 96 g distilled water was added to the substrate-feeding chamber 1. The amount of water added was 60% by weight (being compared with the oil phase substrate). At this time, the water and the soybean oil were separated as lower and upper layers respectively (or separately from each other), to form a clear interface therebetween.

Thereafter, the lower end of the oil phase-removing line 4 (having 3.5 mm of inner diameter) was arranged at a position apart by 10 mm from the upper end of the oil phase. Further, the lower end of the reaction solution-returning line 3 was arranged at a distance of 10 mm upwards from the interface. Thereafter, the oil phase and the aqueous phase were fed by pumps 7 and 6 through the substrate-feeding lines 4 and 5 at flow rates of 5 and 3 g/min., separately from each other. These flow rates were maintained until the reaction was finished, and the aqueous phase was made up to be 60% by weight (being compared with the oil phase).

The reaction solution flowing from returning line 3, when it was discharged from the lower end of the returning line, was separated into an oil phase and an aqueous phase without disturbing the oil-water interface.

As the reaction proceeds, the oil phase became white and turbid due to the emulsification action of monoglycerides formed during decomposition (or hydrolysis), but the interface did not disappear. When the reaction further proceeded, the monoglycerides were further decomposed to form a clear and fine oil phase.

A sample was removed with time from the oil phase in the substrate-feeding chamber 1, and the acid value (AV) and saponification value (SV) were determined, and the degree of decomposition was determined by dividing the acid value with the saponification value. The degree of decomposition of the soybean oil finally reached 96%. Further, the water content in the oil phase just after the reaction was 0.5% as measured by the Karl-Fisher method, and good separation of the oil from water was thus confirmed. FIG. 2 shows a change with time in the degree of decomposition of the oil phase in the circulating stationary separable reactor shown in FIG. 1.

Example 2

20 g of immobilized lipase prepared by immobilizing a lipase (Lipase AY, Amano Pharmaceutical Co., Ltd.) onto ion-exchange resin (Duolite A-568, Diamond Shamrock Co., Ltd.) was charged into a stainless steel column (enzyme column 13 with an inner diameter of 43 mm and a charge height of 47 mm) equipped with a jacket, and kept at 40° C. with the jacket. 1200 g of deionized water was introduced into substrate-feeding chamber 12 (having inner diameter of 132 mm and height of 380 mm), and 2000 g of white soybean-squeezed oil (100% of triglycerides) was added quietly onto the aqueous phase and kept at 40° C. with the jacket. The aqueous phase substrate was fed using pump 20 continuously from the lower end of substrate-feeding chamber 12 to oil-water mixing chamber 14 (with a capacity of 200 ml, stirred at 400 rpm) at a flow rate of 0.24 L/min., and the aqueous substrate overflowed was returned through the reaction solution, aqueous phase returning line 18 to the oil-water separating interface in the substrate-feeding chamber 12. After the temperature of the enzyme column 13, the oil phase substrate and the aqueous phase substrate reached 40° C., the oil phase substrate was fed at 0.24 L/min. using pump 19 from the upper end of the oil phase substrate to the enzyme column 13, to initiate the decomposition. The reaction solution discharged from the enzyme column 13 entered through the reaction solution-discharging line 16 to the oil-water mixing chamber 14 where the reaction solution was mixed with the aqueous phase substrate, and the formed glycerol was transferred to the aqueous phase substrate. Further, a part of the water was transferred by stirring to the oil phase substrate. An overflowed mixture of the reaction solution and the aqueous phase substrate was returned through the reaction solution aqueous phase substrate returning line 18 to the oil-water separating interface in the substrate-feeding chamber 12 where the mixture was left stationarily to be separated into oils and water. This process was repeated continuously, and when the degree of hydrolysis (or decomposition) reached 95%, the reaction was finished. During this operation, the oil phase substrate in the substrate-feeding chamber 12 was sampled periodically, and the degree of decomposition of fats and oils, as well as the water content in the oil phase, was measured. The degree of decomposition of fats and oils was calculated using (acid value/saponification value)×100 (%), and the water content was measured using a water content measuring apparatus (AQUACOUNTER AQ-7, Hiranuma Sangyo Co., Ltd.). The water content in the oil phase substrate in the substrate-feeding chamber 12 was in the range of 0.05 to 2.1%. The operation described above was repeated 4 times. The time elapsed for the degree of hydrolysis to reach 95% in each operation is shown in Table 1.

TABLE 1

| the number of treatments | The time elapsed for the degree of hydrolysis to reach 95% (hr) | |
|---|---|---|
| | Example 2 | Comparative Example 1 |
| 1 | 24 | 24 |
| 2 | 23.9 | 26.3 |
| 3 | 24 | 29.8 |
| 4 | 24 | 32.7 |

Comparative Example 1

Hydrolysis treatment was conducted in the same manner as in Example 2 except that pump 20 was not driven, the aqueous phase substrate was not fed to the oil-water mixing chamber 14, and the contents in the substrate-feeding chamber 12 were stirred at 400 rpm. The mixture of oils and water in the substrate-feeding chamber 12 was sampled and centrifuged at 1000 G for 5 minutes, and from the acid value of the oil phase thus separated, hydrolysis of fats and oils was calculated. The time elapsed for the degree of hydrolysis to reach 95% in each operation is shown in Table 1.

In Example 2, there was little difference in the time elapsed even after the number of treatments was increased, while in Comparative Example 1, the time elapsed was increased as the number of treatments was increased, and the time elapsed in the 4th treatment was longer by about 36% than in Example 2.

Comparative Example 2

Hydrolysis treatment was conducted in the same manner as in Example 2 except that the oil-water mixing chamber 14, the aqueous phase substrate-feeding line 17 and the reaction solution, aqueous phase substrate mixture returning line 18 in Example 2 were not used, and that the end, at the side of the substrate-feeding chamber 12, of the reaction solution-discharging line 16 was arranged in the vicinity of the bottom of the substrate-feeding chamber 12. The degree of decomposition of fats and oils was measured from the acid value in the substrate-feeding chamber 12. The change with time in the degree of this hydrolysis is shown in Table 2.

TABLE 2

| Hydrolysis time (hr) | 2 | 5 | 10 | 24 | 48 |
|---|---|---|---|---|---|
| Degree of hydrolysis (%) | 18 | 58 | 65 | 70 | 72 |

In Example 2, the degree of hydrolysis of 95% was obtained after about 24 hours, while in Comparative Example 2, glycerol in the reaction solution discharged from the enzyme column 13 was poorly extracted in the substrate-feeding chamber 12 so that the reaction was hardly shifted to the side of decomposition and the decomposition (or hydrolysis) time was very long.

The process of the present invention can provide the hydrolysis of fats and oils, which has decomposition (or hydrolysis) rate being equivalent as a conventional hydrolysis process, which shows no reduction of enzyme activity caused by an increase in the number of treatments, and which is stable for a long period of time.

What is claimed is:

1. A batch process for hydrolyzing oil or fat, which comprises the steps:
    a) providing in a substrate-feeding chamber, a liquid oil or fat phase above a liquid aqueous phase such that there is a distinct interface between said phases;
    b) separately removing the liquid oil or fat phase and the liquid aqueous phase from the substrate-feeding chamber, mixing the separately removed liquid oil or fat phase and the liquid aqueous phase, to produce a mixture of the phases, and then feeding said mixture to an immobilized enzyme-containing reaction column, to hydrolyze the oil or fat to produce a reaction mixture containing monoglycerides, diglycerides, fatty acids, glycerol and water;
    c) feeding the reaction mixture to the substrate-feeding chamber, and introducing the mixture into the liquid oil or fat phase therein in a manner such that the interface between the liquid oil or fat phase and the liquid aqueous phase remains distinct and undisturbed, whereby said monoglycerides, diglycerides and fatty acids remain in said liquid oil or fat phase, and said water and glycerol separate into said liquid aqueous phase; and
    d) repeating steps b) and c), until a desired degree of hydrolysis of said oil or fat is obtained, while said interface between said liquid oil or fat and said liquid aqueous phase remains distinct and undisturbed in said substrate-feeding chamber throughout said process.

2. The process of claim 1, wherein the liquid oil or fat phase in the substrate-feeding chamber contains a water content of from saturation to 5% by wt.

3. The process of claim 2, wherein the water content is from saturation to 3% by wt.

4. The process of claim 1, wherein after said hydrolyzing of said oil or fat, said liquid oil or fat phase and said liquid aqueous phase are completely removed, and fresh liquid oil or fat phase and liquid aqueous phase are added to the substrate-feeding chamber for a subsequent batch process according to steps a), b), c) and d).

5. The process of claim 1, wherein said enzyme is selected from the group consisting of lipase or esterase.

6. The process of claim 1, wherein said immobilized enzyme-containing reaction column is heated by a jacket to adjust reaction temperature.

7. The process of claim 2, wherein said liquid oil or fat phase in said substrate-feeding chamber contains a water content which is maintained in a range of 0.05 to 2.1%.

8. The process of claim 1, wherein steps b) and c) are repeated until a 95% degree of hydrolysis is reached.

9. The process of claim 1, wherein in step c), instead of feeding the reaction mixture directly to the substrate-feeding chamber, feeding the reaction mixture from the immobilized enzyme-containing reaction column into a mixing chamber containing liquid aqueous phase fed to the mixing chamber from the substrate-feeding chamber to produce a mixture of the reaction mixture and the liquid aqueous phase, feeding the mixture from the mixing chamber to the substrate-feeding chamber, and introducing the mixture into the liquid oil or fat phase in the same way as the reaction mixture in step c) to maintain said interface distinct and undisturbed, and such that said monoglycerides, diglycerides and fatty acids remain in the liquid oil or fat phase, and said water and glycerol separate into the liquid aqueous phase.

10. A batch process for hydrolyzing oil or fat, which comprises the steps:
   a) providing in a substrate-feeding chamber, a liquid oil or fat phase above an aqueous phase such that there is a distinct interface between said phases;
   b) removing the liquid oil or fat phase from the substrate-feeding chamber, and feeding said liquid oil or fat phase to an immobilized enzyme-containing reaction column, to hydrolyze the oil or fat to produce a reaction mixture containing monoglycerides, diglycerides, fatty acids, glycerol and water;
   c) introducing the reaction mixture from the immobilized enzyme-containing reaction column into a mixing chamber containing liquid aqueous phase fed to the mixing chamber from the substrate-feeding chamber to produce a mixture of the reaction mixture and the liquid aqueous phase,
   d) feeding the mixture produced in step c) to the substrate-feeding chamber and introducing the mixture into the liquid oil or fat phase in such a manner that the interface between the liquid oil or fat phase and the liquid aqueous phase remains distinct and undisturbed, whereby said monoglycerides, diglycerides and fatty acids remain in said liquid oil or fat phase, and said water and glycerol separate into said liquid aqueous phase; and
   e) repeating steps b), c) and d), until a desired degree of hydrolysis of said oil or fat is obtained, while said interface between said liquid oil or fat phase and said liquid aqueous phase remains distinct and undisturbed in said substrate-feeding chamber throughout said process.

11. The process of claim 10, wherein the liquid oil in the substrate-feeding chamber contains a water content of from saturation to 5% by wt.

12. The process of claim 11, wherein the water content is from saturation to 3% by wt.

13. The process of claim 10, wherein after said hydrolyzing of said oil or fat, said liquid oil or fat phase and said liquid aqueous phase are completely removed, and fresh liquid oil or fat phase and liquid aqueous phase are added to the substrate-feeding chamber for a subsequent batch process according to steps a), b), c), d) and e).

14. The process of claim 13, wherein said enzyme is selected from the group consisting of lipase or esterase.

15. The process of claim 10, wherein said immobilized enzyme-containing reaction column is heated by a jacket to adjust reaction temperature.

16. The process of claim 11, wherein said liquid oil or fat phase in said substrate-feeding chamber contains a water content which is maintained in a range of 0.05 to 2.1%.

17. The process of claim 10, wherein steps b) c) and d) are repeated until a 95% degree of hydrolysis is reached.

* * * * *